United States Patent [19]

Lunn

[11] 3,980,644

[45] Sept. 14, 1976

[54] PENTAVALENT PHOSPHORUS AMIDES OF CEPHALOSPORINS AND SEPARATION PROCESS USING SAME

[75] Inventor: William H. W. Lunn, Indianapolis, Ind.

[73] Assignee: Eli Lilly and Company, Indianapolis, Ind.

[22] Filed: Feb. 24, 1975

[21] Appl. No.: 552,093

Related U.S. Application Data

[63] Continuation-in-part of Ser. No. 353,258, April 23, 1973, abandoned, which is a continuation of Ser. No. 105,673, Jan. 11, 1971, abandoned.

[52] U.S. Cl. .............................. 260/243 C; 424/246
[51] Int. Cl.² .............. C07D 501/22; C07D 501/28; C07D 501/40
[58] Field of Search ................................. 260/243 C

[56] References Cited
UNITED STATES PATENTS

| | | | |
|---|---|---|---|
| 3,078,269 | 2/1963 | Koe et al. | 260/239.1 |
| 3,118,878 | 1/1974 | Nayler et al. | 260/239.1 |
| 3,144,444 | 7/1964 | Koe | 260/239.1 |
| 3,558,601 | 1/1971 | Ekström | 260/239.1 |

*Primary Examiner*—Nicholas S. Rizzo
*Assistant Examiner*—Mary C. Vaughn
*Attorney, Agent, or Firm*—William B. Scanlon; Everet F. Smith

[57] ABSTRACT

Novel pentavalent phosphorus amide derivatives of cephalosporin compounds having an amino group substituent (e.g., diethylphosphoramide of cephalosporin C) and a process for recovery of such cephalosporin compounds wherein the pentavalent phosphorus derivatives thereof are extracted with cyclohexanone, and, if desired, precipitated as cyclohexylamine salts.

14 Claims, No Drawings

3,980,644

PENTAVALENT PHOSPHORUS AMIDES OF CEPHALOSPORINS AND SEPARATION PROCESS USING SAME

CROSS REFERENCES

This application is a continuation-in-part of application Ser. No. 353,258, filed Apr. 23, 1973 now abandoned which is a continuation of application Ser. No. 105,673, filed Jan. 11, 1971 now abandoned.

INTRODUCTION

This invention relates to novel pentavalent phosphorus amide derivatives of amino-substituted cephalosporin compounds and to a new and improved method for the separation and/or recovery of such cephalosporin compounds using the phosphoramides.

BACKGROUND OF THE INVENTION

Cephalosporin C-type compounds are frequently derived from cephalosporin C which is prepared by fermentation in accordance with the method described in U.S. Pat. No. 3,093,638, and which is now known to have the structure

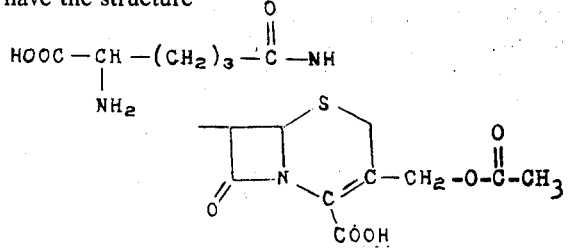

Cephalosporin C is a weak antibiotic but is of more importance as a source of 7-aminocephalosporanic acid, commonly abbreviated 7-ACA. The 7-ACA is prepared by known cleavage processes and is used as an intermediate in the process for preparing a variety of cephalosporin antibiotics, e.g., cephalothin, cephaloridine, and cephaloglycin, which are substantially more potent than cephalosporin C.

Since cephalosporin C is quite valuable in these antibiotic preparation processes, those in the art are seeking more efficient methods for extracting the dissolved cephalosporin C from its fermentation liquor, after separation from the fermentation solids, or from the so-called resin eluate solution containing the cephalosporin C. Resin eluate solutions of cephalosporin C are obtained by passing the filtered fermentation liquor through resin columns which absorb or adsorb the cephalosporin C, and then washing the columns with aqueous liquids which dissolve the cephalosporin C therein.

Efficient methods for extracting greater percentages of the cephalosporin C values from fermentation broths and resin eluate solutions are being developed. For example, Harold B. Hayes et al., U.S. Pat. No. 3,641,018, disclose an improved process for the preparation of 7-ACA from cephalosporin C comprising acylating the amino group in the adipamoyl side chain with an α-halo or α,α-dihalo C$_2$–C$_4$ alkanoyl group, before protecting the carboxyl groups, treating with a halogenating agent to convert the amido group in the 7-position to an imino halide, converting the imino halide to an imino ether, and hydrolyzing the imino ether to 7-aminocephalosporanic acid. That improved method is quite significant but it is also one which commits the operator of the process to the production of 7-aminocephalosporanic acid. There is a need in the cephalosporin art for an alternative process for extracting cephalosporin C and other amine group containing cephalosporins from impure or complex solutions containing them which allows one to regenerate the amine group containing cephalosporin compound.

It is an object of this invention to provide an alternative process for extracting valuable amine group containing cephalosporin compounds from solutions thereof as pentavalent phosphorus amidated derivatives thereof which, if desired, can be easily reversed to the parent amino-group containing cephalosporin compounds.

It is another object of this invention to provide an improved alternative process for obtaining cephalosporin nuclei compounds from the fermentation-derived parent substances.

SUMMARY OF THE INVENTION

This invention provides new pentavalent phosphorus amide derivatives of cephalosporin compounds having free primary amino groups in the molecule.

This invention also provides cyclohexylamine salts of the pentavalent phosphorus amide derivatives of the amino-group containing cephalosporin compounds which form salts with cyclohexylamine.

This invention further provides a process which comprises reacting at a pH above about 7.5 a liquid mixture containing a primary amino-group containing cephalosporin compound with a pentavalent phosphorus halide compound of the formula

wherein X is a halogen, preferably chlorine or bromine, and each of $R_1$ and $R_2$ is selected from the group consisting of -hydrocarbon and -O hydrocarbon radicals which have from 1 to 15 carbon atoms and are free from aliphatic unsaturation to form the pentavalent phosphorus amide of the amino-group containing cephalosporin and then, if desired, extracting the amidated cephalosporin compound into cyclohexanone.

The pentavalent phosphorus amidated cephalosporin compounds in cyclohexanone can be used as intermediates as a means to regenerate the free amino-group containing cephalosporin compound from impure solutions of the same. If this is the option selected, the cyclohexanone solution of the pentavalent phosphorus amide is allowed to stand or is treated at acid or basic pH with a salt forming substance to precipitate the salt. Alternatively, the cyclohexanone solution of the pentavalent phosphorus amide of the amine-group containing cephalosporin compound can be converted to the cyclohexylamine salt. The precipitated cyclohexylamine salt can be separated from the cyclohexanone filtrate by conventional methods and then placed in an appropriate solvent or diluent for further reaction. Thus, for example, the cyclohexylamine salt of the pentavalent phosphorus amide of cephalosporin C can be treated with acetyl chloride in methylene chloride in the presence of a base to form the mixed anhydride of the cephalosporin carboxyl group, and the anhydride can be treated with phosphorus pentachloride to form the imino-chloride, a lower alkanol can be added to form the imino-ether, and water can be added to cleave the side chain to obtain the cephalosporin nucleus compound. These nuclei, for example 7-ACA, are valuable intermediates for use in preparing cephalosporin antibiotic substances such as cephalothin, cephaloridine, and cephaloglycin.

DETAILED DESCRIPTION OF THE INVENTION

The new pentavalent phosphorus compounds are defined by the general formula I

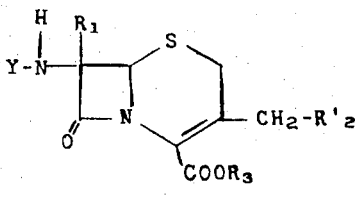

wherein
$R_1$ is hydrogen or methoxyl;
$R'_2$ when taken separately is hydrogen, hydroxy, $C_2$–$C_7$ alkanoyloxy, $C_1$–$C_4$ alkoxy, $C_1$–$C_4$ alkylthio,

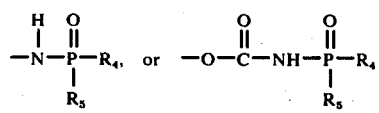

Y is

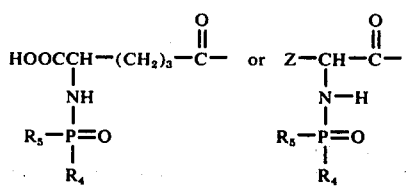

wherein Z is phenyl or 2-thienyl;
wherein each of $R_4$ and $R_5$ is selected from the group consisting of -hydrocarbon and -O-hydrocarbon radicals containing from 1 to 15 carbon atoms, which radicals are free of aliphatic unsaturation; $R_3$ when taken separately is hydrogen, an alkali metal cation, a zinc or cadmium cation, an ammonium or solubilizing amine cation, or a readily removable ester forming group; and $R'_2$ and $R_3$ when taken together form a lactone group of the formula

The compounds of Formula I are valuable intermediates which are useful in the recovery, isolation and purification of amino-substituted cephalosporin compounds. In particular, the compounds of the invention wherein $R_3$ is hydrogen, are especially useful in the form of cyclohexylamine salts.

As is more completely described hereinafter, the cyclohexylamine salts of the foregoing compounds have been found to be relatively insoluble in inert non-hydroxylic solvents and particularly cyclohexanone, and thus these salts permit simple and efficient recovery of the pentavalent phosphorus amide from a cyclohexanone fraction containing that amide. The compounds of this invention are preferably recovered in the form of cyclohexylamine salts since these salts provide for a facile means of separating the antibiotic moiety in a solid pure form.

According to another aspect of this invention there is provided a method for recovering from aqueous media an aminosubstituted cephalosporin compound of the formula II

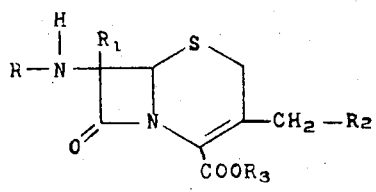

which comprises (a) reacting said cephalosporin compound in said aqueous media at a pH between about pH 7.5 and pH 12 with a phosphorus halide of the formula

to form a pentavalent phosphoramide derivative of the formula I

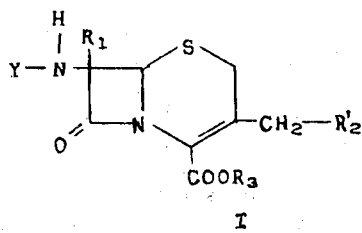

(b) adjusting the pH of the reaction solution to less than pH 5.0, and (c) extracting the cephalosporin phosphoramide derivative from said aqueous media with cyclohexanone, wherein R is hydrogen,

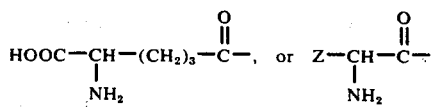

wherein
Z is phenyl or 2-thienyl;
$R_1$ is hydrogen or methoxyl, $R_2$ when taken separately is hydrogen; $C_2$–$C_7$ alkanoyloxy, $C_1$–$C_4$ alkoxy, $C_1$–$C_4$ alkylthio, amino or carbamoyloxy; $R_3$ when taken separately is hydrogen, an alkali metal cation, a zinc or cadmium cation, an ammonium or solubilizing amine cation, or a readily removable ester forming group; and $R'_2$ and $R_3$ when taken together form a lactone group of the formula

and $R_4$ and $R_5$ is selected from the group consisting of -hydrocarbon and -O-hydrocarbon radicals having from 1 to 15 carbon atoms which are free of aliphatic unsaturation, and wherein Y and $R_2'$ have the same meanings as defined for the Formula I.

The amino-group containing cephalosporin starting material can be in the form of the free amino-acid, a water solubilizing salt thereof, a zwitterionic (inner salt) or an ester of such compound. The cephalosporin compound to be used in the process of this invention are often found dissolved in aqueous fermentation liquors or in complex solutions thereof from which it is desired to separate the maximum possible amount of cephalosporin values. It is understood that in some compounds used in this invention, the amino-group may be present as a $-NH_3^+$ group as part of a salt with a corresponding negatively charged chemical moiety either within the compound itself, e.g. (a $COO^-$) or an externally supplied anionic source.

Examples of amino group containing cephalosporin compounds which can be used in the process of this invention include 7-aminocephalosporanic acid (7-ACA), 7-aminodesacetoxycephalosporanic acid (7-ADCA), cephalosporin C, desacetylcephalosporin C, cephalosporin $C_c$, and the like. Also included for use in the process of this invention are the antibiotics A16884, A16886I, and A16886II which are described and claimed in British Pat. No. 1,312,129 and in United States application, Ser. No. 60,556, filed Aug. 3, 1970 (as a continuation-in-part of United States application Ser. No. 847,923, filed Aug. 6, 1969) and in United States application Ser. No. 62,390, filed August 10, 1970 (as a continuation-in-part of application Ser. No. 849,395 filed Aug. 12, 1969). These new antibiotics are now recognized as having the structures:

Examples of other cephalosporin compounds which can be extracted from solutions thereof by the process of this invention include cephaloglycin, cephalexin, and substituted derivatives thereof such as those found in U.S. Pat. Nos. 3,489,750; 3,489,751; and 3,489,752.

U.S. Pat. No. 3,507,861, issued April 21, 1970, claims, among other things, certain 3-methyl-7-α-aminoacylamido-$\Delta^3$-cephem-4-carboxylic acids, e.g., 7-(D-α-aminophenylacetamido)-3-methyl-$\Delta^3$-cephem-4-carboxylic acid, now known generically as cephalexin, an antibiotic.

U.S. application, Ser. No. 571,966, filed Aug. 12, 1966, and the applications parent thereto, disclose certain 7(α-aminoacylamid)-3-acetoxymethyl-$\Delta^3$-cephem-4-carboxylic acids, e.g., 7-(D-α-aminophenylacetamido)-3-acetoxymethyl-$\Delta^3$-cephem-4-carboxylic acid, now known generically as cephaloglycin, and 7[D-α-amino-α-(2'-thienyl)acetamido]-3-acetoxymethyl-$\Delta^3$-cephem-4-carboxylic acid. Other 7-aminoacylamido cephalosporin derivatives which are known to date include 7-(D-α-amino-α-phenylacetamido)3-methoxymethyl-$\Delta^3$-cephem-4-carboxylic acid, and related compounds disclosed in Belgian Pat. No. 719,710, published Feb. 2, 1969 and 7-(D-α-amino-α-phenylacetamido)-3-methylthiomethyl-$\Delta^3$-cephem-4-carboxylic acid, and related compounds disclosed in Belgian Pat. No. 734,532, published Dec. 16; 1969.

The starting materials of the Formula II wherein $R_2$ is amino (3-aminomethyl-3-cephem) are described for example in U.S. Pat. No. 3,274,186, issued Sept. 20, 1966.

Those skilled in the art will recognize that cephalosporin compounds containing amino groups in other parts of the molecule can be separated from complex solutions containing them by the method of this invention. Examples of known aminogroup containing cephalosporin compounds are found in the technical and patent literature. A few citations are given here.

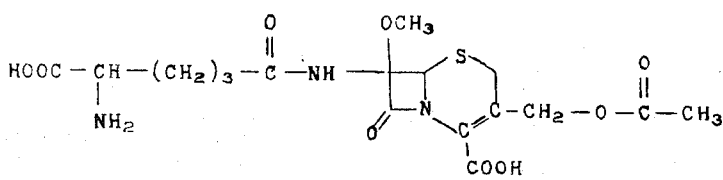

A16884

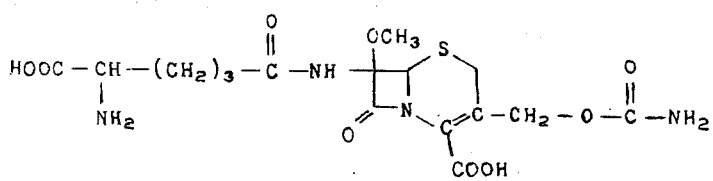

A16886 I

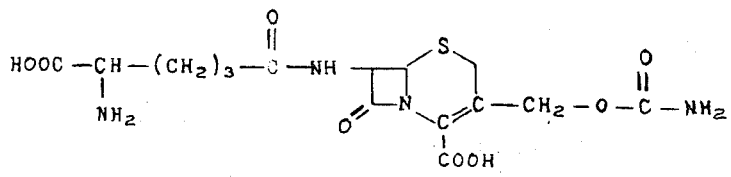

A16886 II

U.S. Pat. No. 3,352,858 names certain 7-α-aminoacylcephalosporin antibiotic compounds, such as 7-[D-α-amino-α-(2'-thienyl)acetamido]-3-methyl-Δ³-cephem-4-carboxylic acid.

U.S. Pat. No. 3,364,212, issued Jan. 16, 1968 discloses some other 7-amino-substituted acyl cephalosporanic acid antibiotics, such as 7-(2-aminooctanamido)cephalosporanic acid, 7-(5-carboxy-2,4-diaminopentanamido)cephalosporanic acid, and 7-(1-aminocyclohexane-1-carboxamido)cephalosporanic acid. Other examples of amine group containing cephalosporins which can be used include:

- the 7-(aminophenyl-acetamido)-cephalosporanic acids, described for example in U.S. Pat. No. 3,422,103, issued Jan. 14, 1969;
- the 7-{2'-[4''-(aminoalkyl)phenyl]acetamide}cephalosporanic and desacetoxycephalosporanic acid compounds described in U.S. Pat. No. 3,382,241, issued May 7, 1968;
- the 7-[D-α-amino-α-(acetamidophenyl)acetamido]-cephalosporanic acids taught by U.S. Pat. No. 3,464,985, issued Sept. 2, 1969, and 7-(aminoalkyl) and 7-(4-amino phenyl)thioacetamidocephalosporanic, desacetoxycephalosporanic, desacetylcephalosporanic acids) and related compounds, e.g. 7-[α-(4-aminophenylthio)acetamido]cephalosporanic acid, disclosed in U.S. Pat. No. 3,422,100, issued Jan. 14, 1969. Such acid compounds dissolved in aqueous media can be extracted therefrom by the process of this invention.

In addition, new pentavalent phosphorus amide derivatives of esters of amino-group containing cephalosporin type compounds can also be made. For example, the 2,2,2-trichloroethyl, benzhydryl, 4-methoxyphenyl and p-nitrobenzyl esters of cephalexin or of 7-ACA or of 7-aminodesacetoxycephalosporanic acid (7-ADCA) can be amidated by the method of this invention. Other esters which can be converted to the pentavalent phosphorus amides according to this invention are:

- the phenacyl, substituted phenacyl, N-phthalimidomethyl and similar esters of 7-ACA, and related compounds disclosed in U.S. Pat. No. 3,284,451, issued Nov. 8, 1966;
- the tert-butyl ester of 7-ACA disclosed in U.S. Pat. No. 3,262,939, issued July 26, 1966, as well as the corresponding esters of any of the above cephalosporin type compound.

In such cases, the ester of the amino-group containing cephalosporin type compound is dissolved in an appropriate inert organic solvent such as the halogenated hydrocarbons, e.g. methylene chloride, dichloroethane, chloroform, or carbon tetrachloride, alkyl alkanoate such as ethyl acetate, propyl acetate, alkanonitriles such as acetonitrile, propionitrile, or the like, and treated with the pentavalent phosphorus halidate of the type described above.

The novel pentavalent phosphorus amides of the present invention are prepared by reacting the cephalosporin compound having an amino group with a pentavalent phosphorus halidate of the formula

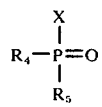

wherein $R_1$ and $R_2$ are as defined above and X is chlorine or bromine. Representative of the phosphorochloridates which can be used in the practice of the invention are diethyl phosphorochloridate, dimethyl phosphorochloridate, diphenyl phosphorochloridate, di-isopropyl phosphorochloridate, di-isobutyl phosphorochloridate, dibutyl phosphorochloridate, as well as a variety of others. The corresponding phosphorobromidates can be used. However, the chloridates are preferred for reasons of economy.

Phosphonohalidates and phosphinohalidates which can be used are exemplified by methyl (methyl)phosphorochloridate, ethyl (ethyl)phosphonochloridate, isopropyl (propyl)phosphonobrimidate, hexyl (hexyl)phosphonochloridates, dodecyl (decyl)phosphonobromidate phenyl (phenyl)phosphonochloridate, phenylethyl (phenylethyl)phosphonochloridate, naphthyl (naphthyl)phosphonochloridate, biphenyl (biphenyl)phosphonochloridate, cyclohexyl (cyclohexyl)phosphonochloridate, dimethylphosphinochloridate, diethylphosphinobromidate, diphenylphosphinochloridate, and the like, as well as such compounds having mixed organic radicals and noninterfering substituents on phenyl ring carbon atoms thereof such as methyl, ethyl, chlorine, nitro, trifluoromethyl or the like.

The pentavalent phosphorus halidates are named herein as derivatives of phosphoric acid, phosphonic acid, or phosphinic acid. Where two organic radicals are bonded to the pentavalent phosphorus through oxygen, the halogenate is termed a phosphorohalogenate. In such compounds, the presence of oxygen is indicated by a space between the organic group and the remainder of the phosphorus compound name. Thus, dimethyl phosphorochloridate means

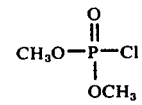

The corresponding pentavalent phosphorus amide made according to this invention, however, would be named for convenience as a "dimethylphosphoramido" compound. Similarly, a phosphonohalidate used in this invention has one organic radical bonded through oxygen to the phosphorus, and one organic radical bonded directly to the phosphorus with a carbon to phosphorus bond. An example is phenyl phenylphosphonobromidate of the structure

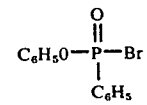

The corresponding pentavalent phosphorus amide obtained therefrom is named herein as a "phenoxy(phenyl)phosphonamido" compound. Likewise, a phosphinohalidate reactant is one having two organic radicals bonded directly to the pentavalent phosphorus atom by carbon to phosphorus bonds. An example is dicyclohexylphosphinochloridate

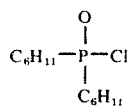

The corresponding pentavalent phosphorus amide is named herein as a "dicyclohexylphosphinamido" compound. Corresponding trivalent phosphorus halidates which are oxidized in the reaction mixture to the pentavalent phosphorus state could also be used if desired.

In preparing the amides of this invention, the amino-group containing cephalosporin of the Formula II is commingled or mixed with the pentavalent phosphorus chloridate or bromidate in at least chemically equivalent proportions relative to the primary amine group content to be amidated, in an appropriate solvent, at a pH above about 7.5 but not so high as to destroy any substantial amount of the β-lactam structure of the cephalosporin. For this reason, the pH is maintained below about 12 and preferable between about 8 and 10. This pH range can be obtained and maintained by the use of a buffer solution. For amidating the acids and salts of amino-group containing cephalosporins, a water containing medium is preferably used. The water may be diluted with any water miscible inert organic solvent. Organic solvents systems are preferred when esters of the amino-group containing cephalosporin compounds are used in the process.

As the inert organic solvent which may be used in combination with or in lieu of water as the reaction medium, use can be made of aliphatic nitriles, such as acetonitrile, etc., aliphatic ketones, such as acetone, methyl ethyl ketone, as well as a variety of others. The reaction temperature is not critical and can be varied within wide ranges. For best results, use should be made of a reaction temperature within the range in of —25° C. to 80° C., and preferably 0° C. to 30° C.

When practicing this process to separate aminogroup containing cephalosporin antibiotics from impure, aqueous mixtures, it is preferred to make use of a starting material in the form of an alkali metal or ammonium salt since the salt form is soluble in water. However, when desired, the free acid may also be used.

Of particular interest as starting materials for the process of this invention are the amino-group containing cephalosporin compounds which are obtained by fermentation and which must be separated from the aqueous fermentation or impure solutions in which they are dissolved or suspended. Examples of such compounds are cephalosporin C and its analogs cephalosporin $C_C$, desacetylcephalosporin C, and the antibiotics A16884, A16886I and A16886II. The amide compounds of this invention which are derivatives of these fermentation derived substances are useful as intermediates for extracting the antibiotic substances from the fermentation media in which they are produced. However, this invention also has applicability to processes for separating any amino-group containing cephalosporin from mixtures in which it may be found. Thus, in some cases, it may be desirable to separate free aminogroup containing cephalosporin esters from reaction media in which they are found. Formation of the amides of those amino-esters in the appropriate organic solvent according to this invention can be used as a step in the overall process of manufacturing antibiotic substances therefrom.

This invention also contemplates new cyclohexanone solutions of the pentavalent phosphorus amides of these aminogroup containing cephalosporin compounds. These solutions can be used as intermediates for separating valuable compounds from crude mixtures thereof, or precursors to valuable antibiotic nuclei. For example, they can be diluted with acidic or basic substances such as aqueous hydrochloric acid to pH 1 to 2 or with aqueous sodium hydroxide to pH 8 to 10, and treated with a basic alkali metal salt such as sodium acetate to reprecipitate or regenerate the alkali metal salt of the amino-group containing cephalosporin compound. As another example, the cyclohexanone solution of the pentavalent phosphorus amide of 7-acylamidocephalosporin compounds can be treated with cyclohexylamine to precipitate the respective cyclohexylamine salt of the amide. The cyclohexylamine salt of the amide can be separated by filtration or centrifugation or other conventional means, mixed into an appropriate organic solvent or diluent, and treated with a carboxylic acyl halide to form the mixed anhydride. The mixed anhydride can be N-deacylated by the known reaction with phosphorus pentachloride in the presence of a base to form the imino chloride, followed by treatment with a $C_1$ to $C_6$ alkanol to form the iminoether, and then with water to cleave the acyl side chain and to obtain the nucleus compound as product. Nuclei compounds such as 7-ACA from cephalosporin C, 7-ADCA from desacetoxycephalosporin C, and the like can be separated from the reaction mixture by precipitation with p-toluenesulfonic acid, as the salt thereof. These nuclei salt compounds can then be reacylated by known procedures to prepare a variety of known antibiotic compounds such as cephalothin, cephaloglycin, cephalexin, and the like.

The cyclohexylamine salts of the pentavalent phosphorus amides of the Formula I are unique in that they form easily handled crystalline precipitates whereas salts of these pentavalent phosphorus amides with a variety of other primary, secondary or tertiary amines are soluble to various degrees, or tend to form oils and gums rather than crystalline solids.

In accordance with the latter aspect of the invention, the cephalosporin compound having an acylamido group containing an amino residue, in the form of the free acid or preferably in the form of a water-soluble salt (e.g., alkali metal or ammonium salt as described above) is recovered from aqueous media by reacting the cephalosporin compound with a pentavalent phosphorus halidate described above at a pH above 7.5, and preferably within the range of 8 to 10, to convert the cephalosporin to the corresponding pentavalent phosphorus amide derivative.

Cyclohexanone is overlayered or otherwise contacted with the resulting aqueous solution, and the whole is stirred or otherwise mixed and adjusted to a pH lower than 5, preferably while cooling to near ice-bath temperatures, e.g., about —10° to about 5°C.) in which condition the pentavalent phosphorus amide derivative is extracted into the cyclohexanone.

It has been found in the practice of the invention that as little as ⅛ volume of cyclohexanone per volume of aqueous solution is sufficient to substantially completely remove the pentavalent phosphorus amide derivative from the aqueous solution. It will be understood that a greater volume of cyclohexanone can be used in this extraction as desired although a dilute solution of the pentavalent phosphorus amide results. For best results, use should be made of a volume of cyclohexanone of 0.30 to 10 parts by volume per part by volume of the aqueous solution of the pentavalent phosphorus amide.

If it is desired to recover the cephalosporin starting material, the cyclohexanone solution containing the pentavalent phosphorus amide is separated from the aqueous phase and allowed to stand for an hour or more at ambient temperatures whereby the cephalosporin starting material precipitates from the solution. Recovery of the cephalosporin starting material can be facilitated by addition of a basic salt, such as an alkali metal acetate (e.g., sodium acetate, potassium acetate, etc.).

Alternatively, the cyclohexanone solution containing the pentavalent phosphorus amide derivative, after separation from the aqueous phase, can be treated with cyclohexylamine whereby the cyclohexylamine salt of the pentavalent phosphorus amide derivative precipitates from solution, which salt can be separated from the wet cyclohexanone by known means.

In some cases, after extended periods of stirring (on the order of 14 to 16 hours) of the wet cyclohexanone suspension of the amide salt, I have observed that in the case of the dialkylphosphoramides, one of the alkyl groups becomes replaced by hydrogen, so that the resulting phosphoramide can be said to be partially hydrolyzed.

As indicated above, the cyclohexylamine salt of the pentavalent phosphorus amide of cephalosporin C, or other related compounds containing a 5-aminoadipoyl group bonded to the amino nitrogen in the 7-position of the cephalosporin, can be used to prepare 7-ACA, or other respective nucleus compound, or to regenerate the corresponding cephalosporin starting material in purer form.

Representative of the compounds of the present invention include the following:

7-[5'-carboxy-5'-(diphenylphosphoramido)-valeramido]-3-acetoxymethyl-$\Delta^3$-cephem-4-carboxylic acid 7-[5'carboxy-5'-(diphenylphosphoramido)-valeramido]-3-propionoxymethyl-$\Delta^3$-cephem-4-carboxylic acid cyclohexylamine salt 7-{5'-carboxy-5'-[phenoxy-(ethyl)phosphonamido]-valeramido}-3-acetoxymethyl-$\Delta^3$-cephem-4-carboxylic acid 7-[5'-carboxy-5'-(dipropylphosphoramido)-valeramido]-3-isobutyryloxymethyl-$\Delta^3$-cephem-4-carboxylic acid 7-[5'-carboxy-5'-(diphenylphosphinamido)-valeramido]-3-methyl-$\Delta^3$-cephem-4-carboxylic acid 7-[5'-carboxy-5'-(diethylphosphinamido)-valeramido]-3-hydroxymethyl-$\Delta^3$-cephem-4-carboxylic acid 7-[D-$\alpha$-(N-diphenyl phosphoramido)-$\alpha$-phenylacetamido]-3-acetoxymethyl-$\Delta^3$-cephem-4-carboxylic acid 7-[5'-carboxy-5'-(dimethylphosphoramido)-valeramido]-3-methyl-$\Delta^3$-cephem-4-carboxylic acid cyclohexylamine salt 7-[5'-carboxy-5'-(diethylphosphoramido)-valeramido]-3-methyl-$\Delta^3$-cephem-4-carboxylic acid 7-[4'-carboxy-4'-(diphenylphosphoramido)-butyrylamido]-3-methyl-$\Delta^3$-cephem-4-carboxylic acid 7-[5'-carboxy-5'-(diphenylphosphoramido)-valeramido]-3-methyl-$\Delta^3$-cephem-4-carboxylic acid 7-[5'-carboxy-5'-(diethylphosphoramido)-valeramido]-3-hydroxymethyl-$\Delta^3$-cephem-4-carboxylic acid 7-[5'-carboxy-5'-(diethylphosphoramido)-valeramido]-3-hydroxymethyl-$\Delta^3$-cephem-4-carboxylic acid cyclohexylamine salt 7-[5'-carboxy-5'-(diethylphosphoramido-valeramido]-3-methyl-$\Delta^3$-cephem-4-carboxylic acid cyclohexylamine salt 7-[5'-carboxy-5'-(diphenylphosphoramido)-valeramido]-cephalosporin $C_c$ 7-[5'-carboxy-5'-(diethylphosphoramido)-valeramido]-7-methoxy-3-acetoxymethyl-$\Delta^3$-cephem-4-carboxylic acid cyclohexylamine salt 7-[5'-carboxy-5'-(diphenylphosphoramido)-valeramido]-7-methoxy-3-acetoxymethyl-$\Delta^3$-cephem-4-carboxylic acid cyclohexylamine salt 7-[5'-carboxy-5'-(diphenylphosphoramido)-valeramido]-7-methoxy-3-carbamyloxymethyl-$\Delta^3$-cephem-4-carboxylic acid 7-[5'-carboxy-5'-(dipropylphosphoramido)-valeramido]-7-methoxy-3-carbamyloxymethyl-$\Delta^3$-cephem-4-carboxylic acid 7-[5'-carboxy-5'-(diethylphosphoramido)-valeramido]-3-carbamyloxymethyl-$\Delta^3$-cephem-4-carboxylic acid cyclohexylamine salt 7-[5'-carboxy-5'-(diphenylphosphoramido)-valeramido]-3-carbamyloxymethyl-$\Delta^3$-cephem-4-carboxylic acid 7-(phenoxyacetamido)-3-(N-dimethylphosphoramidoaminomethyl)-$\Delta^3$-cephem-4-carboxylic acid Having described the basic concepts of the invention, reference is now made to the following examples which are provided by way of illustration, but not by way of limitation, of the practice of the invention.

EXAMPLE 1

Preparation of cyclohexylamine salt of 7-[5'-carboxy-5'-(diphenylphosphoramido)-valeramido]-3-acetoxymethyl-$\Delta^3$-cephem-4-carboxylic acid The monosodium salt of cephalosporin C(68 g. actual assay 84 per cent) is stirred in a solution of 1800 ml. of water and 450 ml. of acetonitrile at a temperature within the range of 13°–16°C. The pH of the solution is adjusted to about 9 by the addition of 15 ml. of a sodium borate buffer formulated as follows:

| | |
|---|---|
| Sodium borate | 210 g. |
| Sodium hydroxide | 63 g. |
| Water | 900 ml. |

Thereafter, diphenyl phosphorochloridate (91 g.), 3375 mm. is added to the reaction mixture and the resulting solution is stirred vigorously while the pH is maintained within the range of 8.6 to 8.8 by the addition of first, 55 ml. of the sodium borate buffer solution and then about 90 ml. of a 25 per cent solution of sodium hydroxide. The reaction temperature is maintained within a range of 13°–16°C. throughout the reaction, or for about 40 minutes.

Thereafter, the pH of the resulting solution is adjusted to about 6.8 by the addition of concentrated hydrochloric acid. The reaction mixture is then cooled by stirring in an ice bath and 600 ml. of cyclohexanone are added to the resulting mixture. The pH is lowered to about 2 by the addition of concentrated hydrochloric acid while the temperature is maintained below 5°C. The entire reaction mixture is then stored in a refrigerator for about 30 minutes after which the upper organic layer is separated from the aqueous layer. The cyclohexanone-containing extract is stirred while cyclohexylamine 44.5 g. (450 mmoles, 3 molar equivalents) is added. After about two-thirds of the cyclohexylamine is added to the reaction mixture, the latter becomes turbid as a result of the addition of the amine. Seed crystals of a cyclohexylamine salt of the diphenylphosphoramide of cephalosporin C from previous smaller scale experiments are added, addition of cyclohexylamine is completed, and the resulting mixture is allowed to stand in an ice bath.

The reaction mixture is then left over night in a refrigerator and the salt separated from the reaction mixture by centrifugation. The product is identified as the cyclohexylamine salt of 7-[5'-carboxy-5'-(diphenylphosphoramido)valeramido]-3-acetoxymethyl-$\Delta^3$-cephem-4-carboxylic acid.

EXAMPLE 2

Preparation of the cyclohexylamine salt of
7-[5'-carboxy-5'-(diethylphosphoramido)
valeramido]-3-acetoxymethyl-$\Delta^3$-cephem-4-carboxylic acid The monosodium salt of cephalosporin C (22.7 g.) is dissolved in 600 ml. of water at a temperature of 13°–16°C. and the pH of the solution is adjusted to about 8.8 using 7 ml. of the sodium borate buffer described in Example 1. Diethyl phosphorochloridate (19.5 g.) is added dropwise with stirring while the temperature of the reaction mixture is maintained at a temperature within the range of 13°–16°C and the pH is maintained at 8.6 to 8.8. Additional quantities of the sodium borate buffer (20 ml.) and then a 25 per cent solution of sodium hydroxide (30 ml.) are added to maintain the pH in the desired range.

Thereafter, the pH of the resulting mixture is adjusted to 6.5 by the addition of concentrated hydrochloric acid (2 ml.) and the entire reaction mixture is cooled with stirring in an ice bath. 150 ml. of cyclohexanone are added to the reaction mixture along with the addition of concentrated hydrochloric acid to lower the pH to about 2. The reaction temperature is maintained at about −10°C. to 5°C.

Thereafter, 2 ml. of cyclohexylamine are added to the cyclohexanone extract which is stirred while cooling. The mixture is placed in a refrigerator for 2 hours after which, the residual oil, after the removal of cyclohexanone, is triturated with acetone and separated by filtration. The product is identified as the cyclohexylamine salt of 7-[5'-carboxy-5'-(diethylphosphoramido)valeramido]-3-acetoxymethyl-$\Delta^3$-cephem-4-carboxylic acid. If the wet cyclohexanone mixture containing the cyclohexylamine salt is allowed to stir at room temperature for 14–16 hours, the product obtained is the cyclohexylamine salt of the monoethylphosphoramido compound.

EXAMPLE 3

Preparation of 7-[5'-carboxy-5'-phenoxy(phenyl)phosphonamido)valeramido]-3-acetoxymethyl-$\Delta^3$-cephem-3-carboxylic acid Using the procedure described in Examples 1 and 2, the monosodium salt of cephalosporin C is reacted with phenoxy(phenyl)phosphonochloridate at a temperature within the range of 13°–16°C. at a pH of about 8.7 using the sodium borate buffer solution described in Example 1.

After the reaction is completed (in just a few minutes) just before acidification, the mixture is cooled to −10°C. to 10°C., and the pH of the resulting reaction mixture is adjusted to about 2 by the addition of concentrated hydrochloric acid and cyclohexanone is added to the reaction mixture.

The organic phase containing the phosphonamide and in cyclohexanone is separated from the aqueous phase, and -(dipropylphosphoramido)valeramido]-phosphonamide is separated from the cyclohexanone. The product is identified as 7-{[5'-carboxy-5'-phenoxy(phenyl)phosphonamido]valeramido}-3-acetoxymethyl-$\Delta^3$-cephem-4-carboxylic acid.

EXAMPLE 4

Preparation of
7-[5'-carboxy-5'-(dipropylphosphoramido)-
valeramido]-3-methyl-$\Delta^3$-cephem-4-carboxylic acid Using the procedure described in Example 3, desacetoxycephalosporin C monosodium salt is reacted with dipropyl phosphorochloridate at a temperature of about 15°C. and a pH of about 8.6 to 8.8. After the reaction is complete, the mixture is cooled as in Example 4, and the pH of the resulting reaction mixture is adjusted to about 3 by means of the addition of concentrated hydrochloric acid, and cyclohexanone is added. The organic phase is then separated from the aqueous phase and the product is identified as 7-[5'-carboxy-5'-dipropylphosphoramido)valeramido]-3-methyl-$\Delta^3$-cephem-4-carboxylic acid.

EXAMPLE 5

Preparation of cyclohexylamine salt of
7-[5'-carboxy-5'-(dimethylphosphoramido)-
valeramido]-3-methyl-$\Delta^3$-cephem-4-carboxylic acid Using the procedure described in Examples 1 and 2, desacetoxycephalosporin C is reacted with dimethyl phosphorochloridate to form the corresponding phosphoramide derivative, which is then extracted with cyclohexanone after cooling. The phosphoramide derivative is then separated from the cyclohexanone by the addition of cyclohexylamine, and the product is recovered by filtration. The product is identified as cyclohexylamine salt of 7-[5'-carboxy-5'-(dimethylphosphoramido)valeramido]-3-methyl-$\Delta^3$-cephem-4-carboxylic acid.

EXAMPLE 6

Preparation of
7-[5'-carboxy-5'-(diphenylphosphoramido)-
valeramido]-3-hydroxymethyl-$\Delta^3$-cephem-4-carboxylic acid Using the procedure described in Example 3, desacetylcephalosporin C monosodium salt is reacted with diphenyl phosphorochloridate at a pH of about 8.7.

After the reaction is completed, the mixture is cooled to −10° to 5°C., and the pH of the reaction mixture is adjusted to 2.

Thereafter, cyclohexanone is added to the reaction mixture and the resulting organic phase is separated from the aqueous phase. The product is identified as 7-[5'-carboxy-5'-(diphenylphosphoramido)-valeramido]-3-hydroxymethyl-$\Delta^3$-cephem-4-carboxylic acid.

EXAMPLE 7

Preparation of cyclohexylamine salt of 7-[5'-carboxy-5'-(diethylphosphinamido)valeramido]-3-hydroxymethyl-$\Delta^3$-cephem-4-carboxylic acid Using the procedure described in Examples 1 and 2, desacetylcephalosporin C is reacted with diethylphosphinochloridate to form the corresponding phosphoramide derivative. The mixture is cooled as in Example 7, and the phosphoramide derivative is then extracted by means of cyclohexanone, and cyclohexylamine is added to the cyclohexanone solution containing the phosphoramide to precipitate the phosphoramide in the form of its cyclohexylamine salt. The product is identified as cyclohexylamine salt of 7-[5'-carboxy-5'-(diethylphosphinamido)valeramido]-3-hydroxymethyl-$\Delta^3$-cephem-4-carboxylic acid.

EXAMPLE 8

Preparation of 7-[5'-carboxy-5'-(diphenylphosphoramido)-valeramido]-3-propionoxymethyl-$\Delta^3$-cephem-4-carboxylic acid Using the procedure described in Example 3, 7-(5'-carboxy-5'-aminovaleramido)-3-propionoxymethyl-$\Delta$3-cephem-4-carboxylic acid monosodium salt is reacted with diphenyl phosphorochloridate in an inert solvent to form the corresponding phosphoramide derivative. The mixture is cooled to −10° to 5°C., and the phosphoramide derivative is then extracted with cyclohexanone, and the product is identified as 7-[5'-carboxy-5'-(diphenylphosphoramido)valeramido]-3-propionoxymethyl-$\Delta^3$-cephem-4-carboxylic acid.

EXAMPLE 9

Preparation of cyclohexylamine salt of 7-[5'-carboxy-5'-(dibenzylphosphoramido)-valeramido]-3-isobutyryloxymethyl-$\Delta^3$-cephem-4-carboxylic acid Using the procedure described in Examples 1 and 2, 7-(5'-carboxy-5'-aminovaleramido)-3-isobutyryloxymethyl-$\Delta^3$-cephem-4-carboxylic acid sodium salt is reacted with dibenzyl phosphorochloridate at a temperature of about 15°C. nd a pH of about 8.9. The reaction mixture is then cooled acidified, and then cyclohexanone is added to extract the phosphoramide derivative from the aqueous solution.

After the removal of the aqueous phase, the resulting cyclohexanone phase is treated with cyclohexylamine whereby the product precipitates from the reaction mixture, and is identified as cyclohexylamine salt of 7-[5'-carboxy-5'-(dibenzylphosphoramido)-valeramido]-3-isobutyryloxymethyl-$\Delta^3$-cephem-4-carboxylic acid.

EXAMPLE 10

Preparation of 7-[5'-carboxy-5'-(diethylphosphoramido)valeramido]-7-methoxy-3-acetoxymethyl-$\Delta^3$-cephem-4-carboxylic acid Using the procedure described in Example 3, 7-(5'-carboxy-5'-aminovaleramido)-7-methoxy-3-acetoxymethyl-$\Delta^3$-cephem-4-carboxylic acid sodium salt is reacted with diethyl phosphorochloridate. The resulting product is then cooled, acidified and extracted with cyclohexanone and the product is identified as 7-[5'-carboxy-5'-(diethylphosphoramido)valeramido]-7-methoxy-3-acetoxymethyl-$\Delta^3$-cephem-4-carboxylic acid.

EXAMPLE 11

Preparation of cyclohexylamine salt of 7-[5'-carboxy-5'-(diphenylphosphoramido)-valeramido]-7-methoxy-3-acetoxymethyl-$\Delta^3$-cephem-4-carboxylic acid Using the procedure described in Examples 1 and 2, 7-(5'-carboxy-5'-aminovaleramido)-7-methoxy-3-acetoxymethyl-$\Delta^3$-cephem-4-carboxylic acid sodium salt is reacted with diphenyl phosphorochloridate to form the corresponding phosphoramide derivative. The mixture is cooled as above and is then extracted from the aqueous reaction mixture with cyclohexanone with acidification. The phosphoramide derivative is separated from the cyclohexanone solution by the addition thereto of cyclohexylamine, and is recovered in the form of the cyclohexylamine salt of 7-[5'-carboxy-5'-(diphenylphosphoramido)valeramido]-7-methoxy-3-acetoxymethyl-$\Delta^3$-cephem-4-carboxylic acid.

EXAMPLE 12

Preparation of 7-[5'-carboxy-5'-phenoxy(phenyl)phosphonamido-valeramido]-7-methoxy-3-carbamyloxymethyl-$\Delta^3$-cephem-4-carboxylic acid Using the procedure described in Example 3, 7-(5'-carboxy-5'-aminovaleramido)-7-methoxy-3-carbamyloxymethyl-$\Delta^3$-cephem-4-carboxylic acid sodium salt is reacted with phenyl phenylphosphonochloridate to form the corresponding phosphonamide derivative which is separated from the aqueous reaction mixture by extraction with cyclohexanone after cooling and acidifying the mixture to a pH below 5. The product is identified as 7-[5'-carboxy-5'-phenoxy(phenyl)phosphonamido-valeramido]-7-methoxy-3-carbamyloxymethyl-$\Delta^3$-cephem-4-carboxylic acid.

EXAMPLE 13

Preparation of cyclohexylamine salt of 7-[5'-carboxy-5'-(diethylphosphoramido)valeramido]-3-carbamyloxymethyl-$\Delta^3$-cephem-4-carboxylic acid Using the procedure described in Examples 1 and 2, 7-(5'-carboxy-5'-aminovaleramido)-3-carbamyloxymethyl-$\Delta^3$-cephem-4-carboxylic acid sodium salt is reacted in aqueous medium with diethyl phosphorochloridate to form the corresponding phosphoramide derivative. The phosphoramide is then extracted from the aqueous reaction mixture with cyclohexanone after cooling and adjusting the pH to below 5 and the phosphoramide derivative is recovered from the cyclohexanone by the addition of cyclohexylamine. The product is identified as the cyclohexylamine salt of 7-[5'-carboxy-5'-(diethylphosphoramido)valeramido]-3-carbamyloxymethyl-Δ³-cephem-4-carboxylic acid.

EXAMPLE 14

Separation of Cephalosporin C

Cephalosporin C sodium salt (22.6 g.) having biological assay of 84.2 per cent is dissolved in a mixture containing 600 ml. of water and 200 ml. of acetonitrile. The solution is then cooled to a temperature of about 15°C. and the pH is adjusted to about 9 by the addition of the sodium borate buffer solution described in Example 1. Thereafter, 23.89 g. (88.6 mm) of diphenyl phosphorochloridate is added over a period of 15 minutes while maintaining the pH at about 9. The reaction mixture is maintained at a pH of about 9 for 1 hour. Thereafter, the reaction mixture is neutralized to a pH of about 6.5 with 30 per cent solution of $H_2SO_4$ and the acetonitrile is removed at a reduced pressure.

200 ml. of cyclohexanone are added and the mixture is cooled at 5°C. and acidified to a pH of 2.0 by further addition of 30 per cent solution of $H_2SO_4$.

The organic phase is separated from the aqueous phase and is labelled Solution A. Thereafter, the remaining aqueous phase is again extracted with 100 ml. of cyclohexanone, and the organic phase separated and labelled Solution B.

Solutions A and B are then separately maintained at a temperature of 40°C. for 4 hours after the addition of 34 ml. of a saturated methanolic solution of sodium acetate was added. In each solution, a precipitate was slowly obtained and was separated by filtration followed by washing with methanol and isopropanol.

Solution A yields 9.32 g. of a product which is identified as sodium cephalosporin C salt and Solution B yields 2.25 g. of a product which is identified as sodium cephalosporin C salt.

EXAMPLE 15

Separation of 7-(5'-carboxy-5'-aminovaleramido)-7-methoxy-3-acetoxymethyl-Δ³-cephem-4-carboxylic acid A sample of 5 g. of 7-(5'-carboxy-5'-aminovaleramido)-7-methoxy-3-acetoxymethyl-Δ³-cephem-4-carboxylic acid having a biological assay of 1750 u/mg. is dissolved in 50 ml. of a mixture of acetonitrile and water in a ratio of 1–3. Thereafter, the pH of the resulting solution is increased from 7.1 to 9.0 by the addition of the sodium borate buffer solution described in Example 1. Thereafter, the solution is cooled to a temperature of 20°C. and 4.3 g (2.5 m) of diphenyl phosphorochloridate are added to the reaction mixture which is then stirred for 60 minutes while the temperature is maintained at 15°–20°C. and the pH is about 9.

Thereafter, the pH of the solution is adjusted to 1.8 by the addition of 5 N HCl, and then extracted with 23 ml. of cyclohexanone.

The cyclohexanone extract is separated from the aqueous phase and held for 5 hours at 30°C. thereafter, 2 volumes of a saturated solution of sodium acetate in methanol are added to the cyclohexanone extract and the resulting mixture is maintained at a temperature of 4°C. overnight.

Thereafter, a precipitate is formed which is separated and identified as sodium 7-(5'-carboxy-5'-aminovaleramido)-7-methoxy-3-acetoxymethyl-Δ³-cephem-4-carboxylate having a biological assay of about 2900 u/mg.

EXAMPLE 16

Separation of 7-(5'-carboxy-5'-aminovaleramido)-7-methoxy-3-carbamyloxymethyl-Δ³-cephem-4-carboxylic acid Using the procedure of Examples 14 and 15, a sample of 7-(5'-carboxy-5'-aminovaleramido)-7-methoxy-3-carbamyloxymethyl-Δ³-cephem-4-carboxylic acid is reacted with phenyl phenylphosphonochloridate to form the corresponding phosphonamide derivative which is then extracted from the aqueous reaction medium into cyclohexanone after cooling to −10° C. to 5° C., and acidifying the mixture to about pH 2.

The cyclohexanone extract is then treated with a saturated solution of sodium acetate in methanol, and the precipitate obtained is identified as 7-(5'-carboxy-5'-aminovaleramido)-7-methoxy-3-carbamyloxymethyl-Δ³-cephem-4-carboxylic acid. Biological assay indicates that the purity of the product is comparable to Example 15.

EXAMPLE 17

Preparation of 7-aminocephalosporanic acid

A sample of 12.7 g. of the cyclohexylamine salt of 7-[5'-carboxy-5'-(diethylphosphoramido)valeramido]-3-acetoxymethyl-Δ³-cephem-4-carboxylic acid sodium salt is formulated into a reaction mixture containing 50 ml. of methylene chloride, 14.5 ml. of diethyl-aniline and 10.6 ml. of acetyl chloride. The resulting mixture is then cooled to about −15°C. and stirred for 1 hour. Thereafter, an additional 14.5 g. of diethyl-aniline are added. Thereafter, a solution containing 100 ml. of methylene chloride and 12.0 g. of phosphorus pentachloride are added to the mixture and the resulting mixture is cooled at −15°C. for 90 minutes. Thereafter, 50 ml. of methanol and the resulting reaction mixture are stirred at a temperature less than −15°C. for 60 minutes. Next, 100 ml. of water are added and the reaction mixture is stirred for 15 minutes in an ice bath. The aqueous phase is separated from the organic phase, and the pH of the aqueous phase is adjusted from 0.4 to 3.6 with 14 ml. of concentrated ammonium hydroxide. The solution is stirred for 30 minutes, filtered and washed with 20 ml. of a 50 per cent solution of methanol in water, followed by 20 ml. of acetone. The product is then filtered and dried and is identified as 7-aminocephalosporanic acid.

EXAMPLE 18

Preparation of 7-amino-3-carbamyloxymethyl-Δ³-cephem-4-carboxylic acid

A sample of 7-[5'-carboxy-5'-isopropoxy(isopropyl)-phosphonamido-valeramido]-3-carbamyloxymethyl-Δ³-cephem-4-carboxylic acid cyclohexylamine salt is reacted with $PCl_5$, methanol and water in accordance with the procedure of Example 17. The product is separated in the manner described in Example 17 and identified as 7-amino-3-carbamyloxymethyl-Δ³-cephem-4-carboxylic acid.

I claim:
1. The cephalosporin pentavalent phosphorus amide derivative of the formula

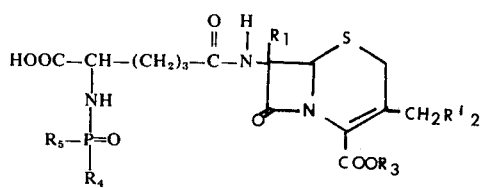

wherein
R₁ is hydrogen or methoxyl;
R'₂ when taken separately is hydrogen, hydroxy, acetoxy,

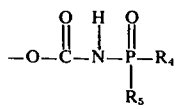

R₃ when taken separately is hydrogen, an alkali metal cation, or a zinc or cadmium cation,
R'₂ and R₃ when taken together from a the group consisting of of the formula

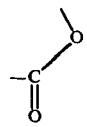

R₄ and R₅ are each selected from the group consisting of -hydrocarbon and —O-hydrocarbon radicals containing from 1 to 15 carbon atoms, which radicals are free of aliphatic unsaturation;
and when R₃ is hydrogen, the cyclohexylamine salts thereof.

2. The compound of claim 1 wherein each of R₄ and R₅ is phenyl; R₃ is hydrogen or an alkali metal cation; and R'₂ is acetoxy.

3. The cyclohexylamine salt of the compound of claim 2.

4. The compound of claim 1 wherein R'₂ is a group of the formula

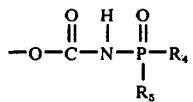

wherein each of R₄ and R₅ is phenyl; and R₃ is hydrogen or an alkali metal cation.

5. The cyclohexylamine salt of the compound of claim 4.

6. The process for recovering from aqueous media a cephalosporin compound of the formula

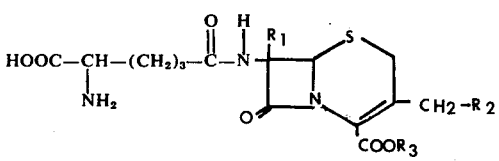

which comprises
a. reacting said cephalosporin compound in said aqueous media at a pH between about pH 7.5 and pH 12 with a phosphorus halide of the formula

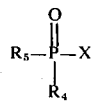

to form a pentavalent phosphoramide derivative of the formula

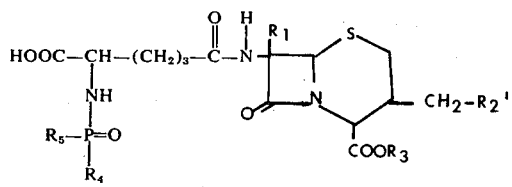

a. adjusting the pH of the reaction solution to less than pH 5.0 and
c. extracting the cephalosporin phosphoramide from said reaction solution with cyclohexanone;
wherein R₁ is hydrogen or methoxyl;
R₂ when taken separately is hydrogen, hydroxy, acetoxy, or carbamoyloxy;
R₂' when taken separately is hydrogen, hydroxy, acetoxy, or a group of the formula

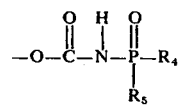

R₃ when taken separately is hydrogen, an alkali metal cation, or a zinc or cadmium cation;
R₂ and R₃ when taken together form a lactone group of the formula

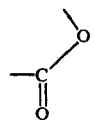

and R₄ and R₅ are each selected from the group consisting of -hydrocarbon and -O-hydrocarbon radicals containing from 1 to 15 carbon atoms which radicals are free of aliphatic unsaturation.

7. The process as defined in claim 6 which further includes the step of adding cyclohexylamine to the cyclohexanone extract to precipitate the cephalosporin pentavalent phosphoramide derivative as the cyclohexylamine salt.

8. The process as defined in claim 6 which further includes the step of hydrolyzing the cephalosporin phosphoramide derivative at room temperature.

9. The process of claim 6 wherein R₁ is hydrogen.

10. The process of claim 9 wherein the cephalosporin compound is a 7-(5'-carboxy-5'-aminovaleramido)-3-acetoxymethyl-Δ³-cephem-4-carboxylic acid salt.

11. The process of claim 9 wherein the cephalosporin compound is a 7-(5'-carboxy-5'-aminovaleramido)-3- carbamoyloxymethyl-Δ³-cephem-4-carboxylic acid salt.

12. The process of claim 6 wherein $R_1$ is methoxyl.

13. The process of claim 12 wherein the cephalosporin compound is a 7-(5'-carboxy-5'-aminovaleramido)-7-methoxy-3-acetoxymethyl-Δ³-cephem-4-carboxylic acid salt.

14. The process of claim 12 wherein the cephalosporin compound is a 7-(5'-carboxy-5'-carboxy-5'-aminovaleramido)-7-methoxy-3-carbamoyloxymethyl-Δ³-cephem-4-carboxylic acid salt.

* * * * *